United States Patent
Ogawa et al.

(10) Patent No.: US 9,993,144 B2
(45) Date of Patent: Jun. 12, 2018

(54) CONTROL METHOD FOR ENDOSCOPE REPROCESSOR

(71) Applicant: OLYMPUS CORPORATION, Tokyo (JP)

(72) Inventors: Akihisa Ogawa, Hachioji (JP); Hiromasa Akahori, Tachikawa (JP)

(73) Assignee: OLYMPUS CORPORATION, Tokyo (JP)

( * ) Notice: Subject to any disclaimer, the term of this patent is extended or adjusted under 35 U.S.C. 154(b) by 0 days. days.

(21) Appl. No.: 15/450,530

(22) Filed: Mar. 6, 2017

(65) Prior Publication Data

US 2017/0172395 A1 Jun. 22, 2017

Related U.S. Application Data

(63) Continuation of application No. PCT/JP2016/059494, filed on Mar. 24, 2016.

(30) Foreign Application Priority Data

Jun. 5, 2015 (JP) ................................. 2015-114990

(51) Int. Cl.
*A61L 2/18* (2006.01)
*A61B 1/12* (2006.01)
(Continued)

(52) U.S. Cl.
CPC ................ *A61B 1/121* (2013.01); *A61L 2/18* (2013.01); *A61L 2/24* (2013.01); *A61L 2/26* (2013.01);
(Continued)

(58) Field of Classification Search
CPC ... A61B 1/121; A61L 2/18; A61L 2/24; A61L 2/26; A61L 2202/14; A61L 2202/17; A61L 2202/24; G01N 27/416
See application file for complete search history.

(56) References Cited

U.S. PATENT DOCUMENTS

| 9,661,999 B2* | 5/2017 | Akahori | A61L 2/18 |
| 2008/0267812 A1* | 10/2008 | Kawachi | A61L 2/18 |
| | | | 422/3 |
| 2017/0079516 A1* | 3/2017 | Akahori | A61L 2/18 |

FOREIGN PATENT DOCUMENTS

| JP | S63-292056 A | 11/1988 |
| JP | 2000-329728 A | 11/2000 |

(Continued)

OTHER PUBLICATIONS

International Search Report dated Jun. 21, 2016 issued in PCT/JP2016/059494.

(Continued)

*Primary Examiner* — Timothy C Cleveland
(74) *Attorney, Agent, or Firm* — Scully, Scott, Murphy & Presser, P.C.

(57) ABSTRACT

A control method for an endoscope reprocessor including a medicinal solution tank, a concentration measurement chamber, and a concentration meter disposed in the concentration measurement chamber and which comprises a container, an electrode housed inside the container, a permeable membrane sealing the container, and a content fluid sealed inside the container, the control method, includes: a step I of introducing a medicinal solution into the medicinal solution tank; a step II of introducing the medicinal solution into the concentration measurement chamber and measuring a concentration of the medicinal solution; a step III of draining the medicinal solution inside the medicinal solution tank from the endoscope reprocessor, and maintaining a state where inside of the medicinal solution tank is empty for a predetermined time period; and a step IV of maintaining a moisture content inside the concentration measurement chamber at a predetermined value or more during the step III.

5 Claims, 6 Drawing Sheets

(51) Int. Cl.
  *A61L 2/24* (2006.01)
  *A61L 2/26* (2006.01)
  *G01N 27/416* (2006.01)

(52) U.S. Cl.
  CPC ........ *G01N 27/416* (2013.01); *A61L 2202/14* (2013.01); *A61L 2202/17* (2013.01); *A61L 2202/24* (2013.01)

(56) References Cited

FOREIGN PATENT DOCUMENTS

| | | |
|---|---|---|
| JP | 2010-057792 A | 3/2010 |
| JP | 2010-057793 A | 3/2010 |
| JP | 2010-119592 A | 6/2010 |
| JP | 2013-064702 A | 4/2013 |
| JP | 5826982 B1 | 12/2015 |
| JP | 5893817 B1 | 3/2016 |
| WO | WO 2016/035377 A1 | 3/2016 |

OTHER PUBLICATIONS

Extended Supplementary European Search Report dated Mar. 14, 2018 in European Patent Application No. 16 80 2887.6.

\* cited by examiner

CONTROL METHOD FOR ENDOSCOPE REPROCESSOR

CROSS REFERENCE TO RELATED APPLICATION

This application is a continuation application of PCT/JP2016/059494 filed on Mar. 24, 2016 and claims benefit of Japanese Application No. 2015-114990 filed in Japan on Jun. 5, 2015, the entire contents of which are incorporated herein by this reference.

BACKGROUND OF THE INVENTION

1. Field of the Invention

The present invention relates to a control method for an endoscope reprocessor that includes a concentration meter.

2. Description of the Related Art

Endoscopes used in the medical field are subjected to reprocessing, such as a cleaning treatment and a disinfecting treatment, using a medicinal solution after use. In addition, endoscope reprocessors that automatically perform reprocessing of endoscopes are known. For example, Japanese Patent Application Laid-Open Publication No. 2010-57792 discloses an endoscope reprocessor that includes a medicinal solution tank which accumulates a medicinal solution and in which a concentration meter is provided that is configured to measure a concentration of a medicinal solution that is used for reprocessing.

A concentration meter of a form that uses a permeable membrane which allows the passage of specific ions contained in a medicinal solution is known. When measuring the concentration of a medicinal solution using the form of the concentration meter, the medicinal solution is caused to contact with a measuring surface that is a part at which the permeable membrane is provided.

SUMMARY OF THE INVENTION

A control method for an endoscope reprocessor according to one aspect of the present invention is a control method for an endoscope reprocessor including a medicinal solution tank, a concentration measurement chamber, and a concentration meter which is disposed in the concentration measurement chamber and which comprises a container, an electrode that is housed inside the container, a permeable membrane configured to seal the container, and a content fluid that is sealed inside the container, the control method including: a step I of introducing a medicinal solution into the medicinal solution tank; a step II of introducing the medicinal solution into the concentration measurement chamber and measuring a concentration of the medicinal solution; a step III of draining the medicinal solution inside the medicinal solution tank from the endoscope reprocessor, and maintaining a state in which inside of the medicinal solution tank is empty for a predetermined time period; and a step IV of maintaining a moisture content inside the concentration measurement chamber at a predetermined value or more during the step III.

DETAILED DESCRIPTION OF THE PREFERRED EMBODIMENT(S)

Figure 1:
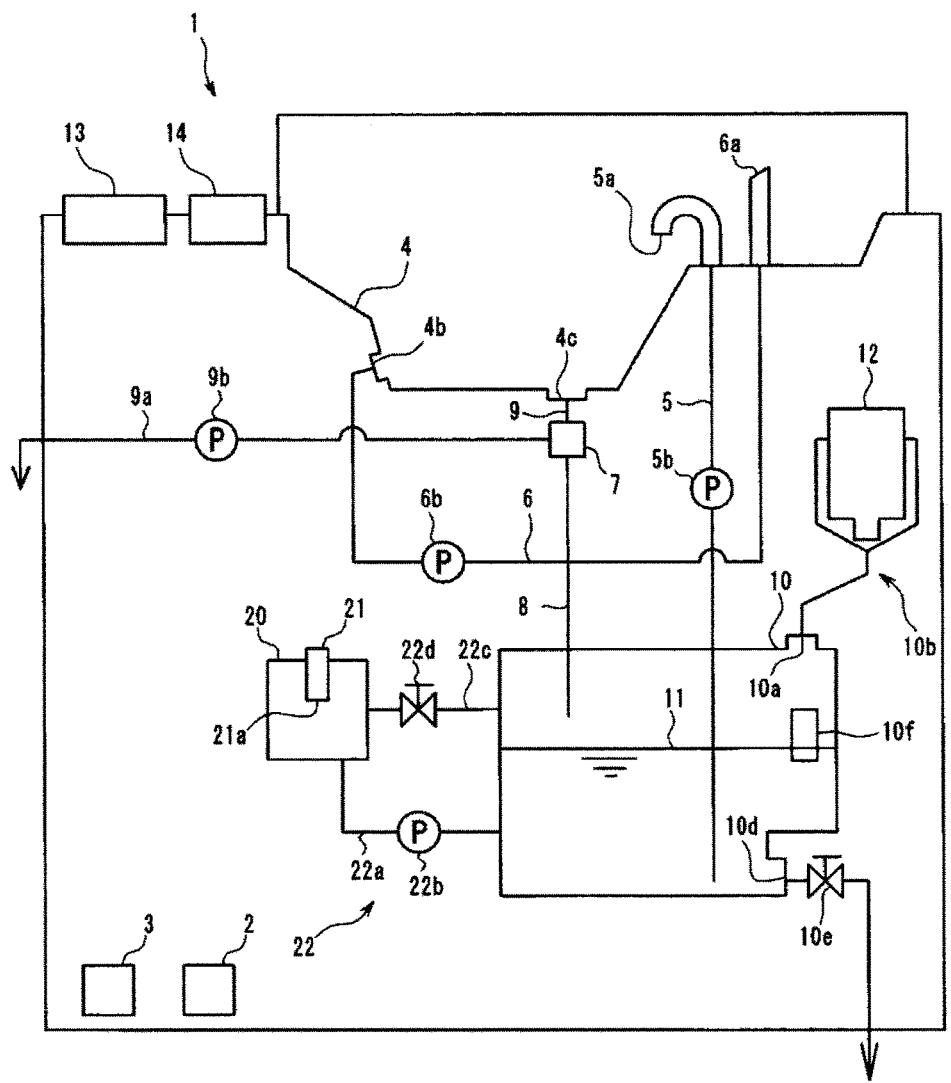
FIG. 1 is a view illustrating a schematic configuration of an endoscope reprocessor according to a first embodiment.

Preferred embodiments of the present invention are described hereunder with reference to the accompanying drawings. Note that the respective components in the respective drawings used for the following description are displayed in a different contraction scale so as to be shown in a size that is recognizable in the drawings, and the present invention is not limited only to the quantity of components, the shapes of components, the ratios between the sizes of components, and the relative positional relationship between the respective components illustrated in the drawings.

First Embodiment

Hereunder, an example of an embodiment of the present invention is described. An endoscope reprocessor 1 illustrated in FIG. 1 is an apparatus that performs reprocessing with respect to an endoscope. The reprocessing referred to here is not particularly limited, and may be any one of, or a combination of any two or more of, the following: a rinsing treatment using water, a cleaning treatment that removes dirt such as organic matter, a disinfecting treatment that nullifies predetermined microorganisms, and a sterilization treatment that eliminates or kills all microorganisms.

As one example according to the present embodiment, a disinfecting treatment using a medicinal solution 11 that is a disinfecting liquid is included in the reprocessing which the endoscope reprocessor 1 performs. The endoscope reprocessor 1 includes a control portion 2, a power supply portion 3, a treatment tank 4, a medicinal solution tank 10, a concentration measurement chamber 20 and a concentration meter 30.

The control portion 2 is configured to include an arithmetic unit (CPU), a storage apparatus (RAM), an auxiliary storage apparatus, an input/output apparatus and a power control apparatus and the like, and may have a configuration that controls operations of each part configuring the endoscope reprocessor 1 based on a predetermined program. In the following description, the operations of each component included in the endoscope reprocessor 1 are controlled by the control portion 2 even when no specific description to that effect exists.

The power supply portion 3 supplies power to each part of the endoscope reprocessor 1. As one example according to the present embodiment, the power supply portion 3 distributes power that is obtained from outside, such as from a commercial power source, to each part. Note that the power supply portion 3 may also include a power generating apparatus or a battery.

The treatment tank 4 is a concave shape having an opening portion that is open and is capable of accumulating a liquid therein. An unshown endoscope can be disposed inside the treatment tank 4. A configuration may also be adopted in which an opening at an upper part of the treatment tank 4 can be closed with a lid. A medicinal solution nozzle 5a and a drain port 4c are provided inside the treatment tank 4.

The medicinal solution nozzle 5a is an opening portion that communicates with the medicinal solution tank 10 through a medicinal solution conduit 5. The medicinal solution tank 10 accumulates the medicinal solution 11. Although the kind of the medicinal solution 11 that the medicinal solution tank 10 accumulates is not particularly limited, as described above the medicinal solution 11 of the present embodiment is a disinfecting liquid such as peracetic acid that is used in a disinfecting treatment. Note that the medicinal solution 11 may also be a cleaning liquid that is used in a cleaning treatment or the like. A medicinal solution pump 5b is provided in the medicinal solution conduit 5. By operating the medicinal solution pump 5b, the medicinal solution 11 inside the medicinal solution tank 10 is transferred to inside the treatment tank 4.

The drain port 4c is an opening portion that is provided at the lowest place inside the treatment tank 4. The drain port 4c is connected to a discharge conduit 9. The discharge conduit 9 communicates with the drain port 4c and a switching valve 7. A recovery conduit 8 and a disposal conduit 9a are connected to the switching valve 7. The switching valve 7 is switchable among a state in which the switching valve 7 blocks the discharge conduit 9, a state in which the switching valve 7 allows the discharge conduit 9 and the recovery conduit 8 to communicate, and a state in which the switching valve 7 allows the discharge conduit 9 and the disposal conduit 9a to communicate.

The recovery conduit 8 communicates the medicinal solution tank 10 and the switching valve 7. A discharge pump 9b is provided in the disposal conduit 9a. The disposal conduit 9a is connected with drainage equipment for receiving liquid discharged from the endoscope reprocessor 1.

When the switching valve 7 is placed in a closed state, liquid can be accumulated inside the treatment tank 4. Further, at a time that the medicinal solution 11 is accumulated inside the treatment tank 4, the medicinal solution 11 is transferred from the treatment tank 4 to the medicinal solution tank 10 by placing the switching valve 7 in a state that allows the discharge conduit 9 and the recovery conduit 8 to communicate. Furthermore, by placing the switching valve 7 in a state that allows the discharge conduit 9 and the disposal conduit 9a to communicate and starting operation of the discharge pump 9b, liquid inside the treatment tank 4 is sent to the drainage equipment via the disposal conduit 9a.

A circulation port 4b and a circulation nozzle 6a are also provided inside the treatment tank 4. The circulation port 4b and the circulation nozzle 6a communicate with each other through a circulation conduit 6. A circulation pump 6b is provided in the circulation conduit 6.

By operating the circulation pump 6b, the liquid inside the treatment tank 4 is sucked out from the circulation port 4b and thereafter returns into the treatment tank 4 via the circulation conduit 6 and the circulation nozzle 6a. The endoscope reprocessor 1 houses an endoscope inside the treatment tank 4, and executes a disinfecting treatment or the like on the endoscope by circulating the medicinal solution 11 that is accumulated in the treatment tank 4.

A medicinal solution introduction port 10a, a medicinal solution discharge port 10d and a liquid level gauge 10f are provided in the medicinal solution tank 10. The medicinal solution introduction port 10a is an opening portion that is provided in the medicinal solution tank 10. The medicinal solution introduction port 10a communicates a medicinal solution supply portion 10b.

The medicinal solution supply portion 10b supplies the medicinal solution 11 to the medicinal solution tank 10. As one example according to the present embodiment, the medicinal solution supply portion 10b has a configuration that communicates with a medicinal solution bottle 12 in which the medicinal solution 11 which is unused is stored and the medicinal solution introduction port 10a. By connecting the medicinal solution bottle 12 to the medicinal solution supply portion 10b, the unused medicinal solution 11 can be introduced into the medicinal solution tank 10 from the medicinal solution bottle 12 via the medicinal solution supply portion 10b and the medicinal solution introduction port 10a.

The medicinal solution discharge port 10d is an opening portion that is provided at the bottom of the medicinal solution tank 10. A discharge valve 10e that is configured to open and close the medicinal solution discharge port 10d is provided in the medicinal solution discharge port 10d.

When the discharge valve 10e is placed in a closed state, the medicinal solution 11 can be accumulated inside the medicinal solution tank 10. Further, when the discharge valve 10e is placed in an open state, the medicinal solution 11 inside the medicinal solution tank 10 can be discharged from the endoscope reprocessor to thereby place the inside of the medicinal solution tank 10 in an empty state. However, a configuration may also be adopted in which the medicinal solution discharge port 10d and the discharge valve 10e are not provided. In this case, the inside of the medicinal solution tank 10 can be placed in an empty state by transferring the medicinal solution to the treatment tank 4 through the medicinal solution conduit 5, and discharging the medicinal solution from inside the treatment tank 4 via the drain port 4c and the disposal conduit 9a.

The liquid level gauge 10f detects whether or not the liquid surface of the medicinal solution 11 accumulated inside the medicinal solution tank 10 reaches a predetermined height inside the medicinal solution tank 10. The liquid level gauge 10f is electrically connected to the control portion 2, and outputs information regarding a detection result to the control portion 2.

The configuration of the liquid level gauge 10f is not particularly limited. For example, the liquid level gauge 10f may be a so-called "electrode-type liquid level sensor" that includes a pair of electrodes which are arranged apart from each other, and that is configured to detect whether or not the medicinal solution 11 reaches a predetermined liquid level based on the presence or absence of electrical conductivity between the pair of electrodes. Alternatively, for example, the liquid level gauge 10f may be a so-called "float-type liquid level sensor" that is configured to detect whether or not the medicinal solution 11 reaches a predetermined liquid level based on the operating state of a switch that opens/closes in accordance with vertical movement of a float that floats in the medicinal solution 11.

Note that the medicinal solution tank 10 may also have a configuration that introduces tap water and mixes the tap water and a medicinal solution at a predetermined ratio.

The concentration measurement chamber 20 has an internal space that accumulates the medicinal solution 11. A medicinal solution transfer portion 22 is connected to the concentration measurement chamber 20. The medicinal solution transfer portion 22 transfers the medicinal solution 11 bidirectionally between the medicinal solution tank 10 and the concentration measurement chamber 20. The medicinal solution transfer portion 22 also seals the internal space of the concentration measurement chamber 20. A measuring surface 21a of a concentration meter 21 that is described later is disposed inside the concentration measurement chamber 20.

Although the configuration of the medicinal solution transfer portion 22 is not particularly limited, as one example according to the present embodiment the medicinal solution transfer portion 22 includes an introduction conduit 22a, an introducing pump 22b, a lead-out conduit 22c and an open/close valve 22d.

The introduction conduit 22a and the lead-out conduit 22c communicate the medicinal solution tank 10 and the concentration measurement chamber 20. A part of the opening provided in the concentration measurement chamber 20 that is a part which excludes the opening portion that communicates with the introduction conduit 22a and the lead-out conduit 22c is temporarily or permanently sealed.

The introducing pump 22b is provided in the introduction conduit 22a. When in an operating state, the introducing pump 22b transfers a fluid that is inside the introduction conduit 22a in the direction from the medicinal solution tank 10 toward the concentration measurement chamber 20. The introducing pump 22b is a so-called "self-priming type pump". The introducing pump 22b has a configuration that prevents a fluid inside the introduction conduit 22a from flowing towards the medicinal solution tank 10 from the concentration measurement chamber 20 when the introducing pump 22b is in a stopped state.

The open/close valve 22d is provided in the lead-out conduit 22c, and opens and closes the lead-out conduit 22c. Opening and closing operations of the open/close valve 22d are controlled by the control portion 2. The open/close valve 22d is configured to maintain a closed state when the power of the endoscope reprocessor 1 is in an "off" state.

In a state in which the medicinal solution 11 is accumulated inside the medicinal solution tank 10, the medicinal solution 11 inside the medicinal solution tank 10 is introduced into the concentration measurement chamber 20 by placing the open/close valve 22d in an open state and operating the introducing pump 22b. In addition, after the medicinal solution 11 has been introduced into the concentration measurement chamber 20, by placing the open/close valve 22d in an open state and operating the introducing pump 22b, the medicinal solution 11 circulates so as to return to the medicinal solution tank 10 via the medicinal solution tank 10, the introduction conduit 22a, the concentration measurement chamber 20 and the lead-out conduit 22c.

Further, the inside of the concentration measurement chamber 20 is sealed by placing the introducing pump 22b in a stopped state and placing the open/close valve 22d in a closed state.

Note that, the open/close valve 22d is not limited to the form of an electric motor-driven valve in which operations to open and close are controlled by the control portion 2. For example, the open/close valve 22d may be a relief valve that is configured to enter an open state when a pressure difference between the pressure of a fluid in the lead-out conduit 22c on the medicinal solution tank 10 side thereof and the pressure of a fluid in the lead-out conduit 22c on the concentration measurement chamber 20 side thereof exceeds a predetermined value. Further, the open/close valve 22d may be a check valve that is configured to allow fluid inside the lead-out conduit 22c to flow from the concentration measurement chamber 20 toward the medicinal solution tank 10 and prevent fluid flowing from the medicinal solution tank 10 toward the concentration measurement chamber 20. In a case where the open/close valve 22d is a relief valve or a check valve, the inside of the concentration measurement chamber 20 can be sealed by placing the introducing pump 22b in a stopped state.

Note that the configuration of the medicinal solution transfer portion 22 is not limited to the configuration in the present embodiment. For example, the medicinal solution transfer portion 22 may be configured by a single conduit that allows the medicinal solution tank 10 and the concentration measurement chamber 20 to communicate with each other, a pump that is provided in the conduit and is capable of bidirectionally transferring fluid inside the conduit, and an open/close valve that is configured to open and close the conduit.

Furthermore, for example, the medicinal solution transfer portion 22 may include a conduit that allows the medicinal solution tank 10 and the concentration measurement chamber 20 to communicate with each other, and an open/close valve that is configured to open and close the conduit, and may have a configuration that, without using a pump, transfers the medicinal solution 11 bidirectionally between the medicinal solution tank 10 and the concentration measurement chamber 20 by means of a liquid level difference between the medicinal solution tank 10 and the concentration measurement chamber 20.

The concentration meter 21 includes the measuring surface 21a that is disposed inside the concentration measurement chamber 20. The concentration meter 21 measures the concentration of the medicinal solution 11 that contacts the measuring surface 21a.

The configuration of the concentration meter 21 is not particularly limited as long as the concentration meter 21 is capable of measuring the concentration of a specific substance contained in the medicinal solution 11.

Figure 2:
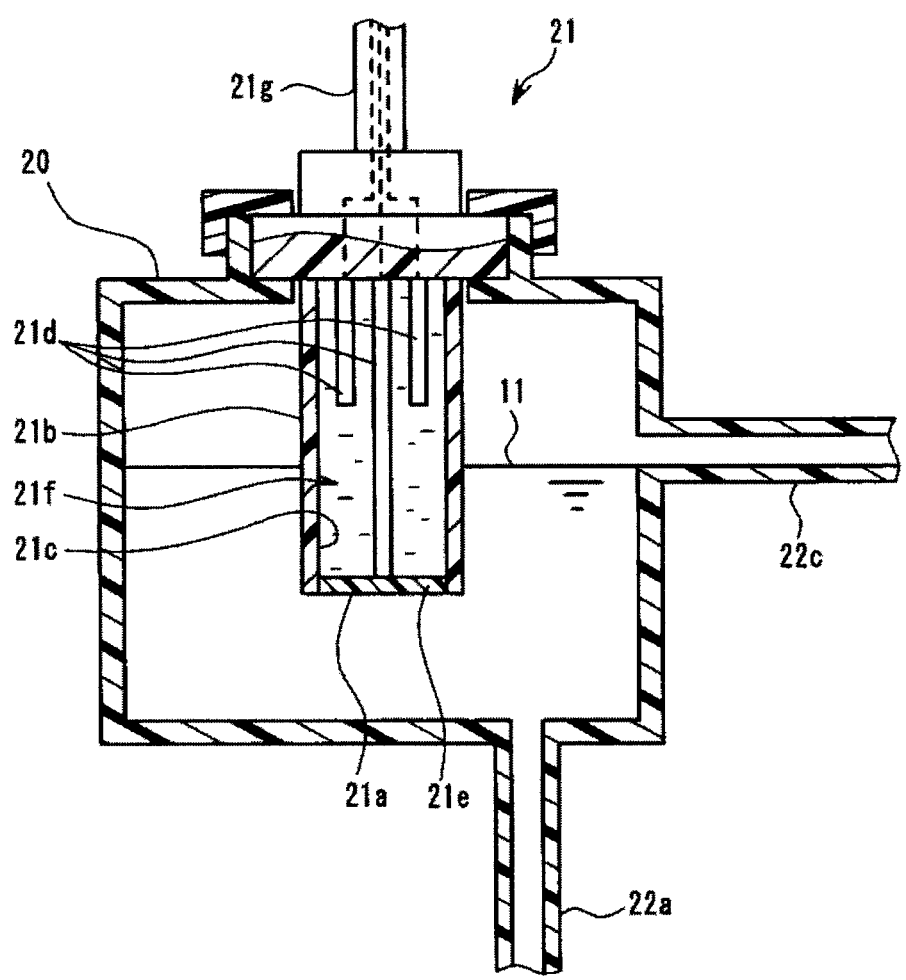
FIG. 2 is a cross-sectional diagram illustrating the configuration of a concentration measurement chamber and a concentration meter according to the first embodiment.

As shown in FIG. 2, as one example according to the present embodiment, the measuring surface 21a is one part of the outer surface of a measurement portion 21b. The measurement portion 21b is a container-like member in which an opening portion 21c is provided. The opening portion 21c is sealed by a permeable membrane 21e. A content fluid 21f is sealed inside the opening portion 21c of the measurement portion 21b.

The measuring surface 21a is a surface on an opposite side to a region which contacts the content fluid 21f of the permeable membrane 21e. The permeable membrane 21e allows a specific substance contained in the medicinal solution 11 that contacts the measuring surface 21a to pass to the content fluid 21f side. That is, the concentration of the substance in the content fluid 21f changes in accordance with the concentration of the substance in the medicinal solution 11 that contacts the measuring surface 21a.

In the measurement portion 21b, a plurality of electrodes 21d are arranged apart from each other within the content fluid 21f. The plurality of electrodes 21d are connected to an unshown control apparatus through an electrical cable 21g. Note that the control apparatus may also be configured integrally with the measurement portion 21b.

The concentration meter 21 measures a difference in potential that arises among the plurality of electrodes 21d immersed in the content fluid 21f or a change in a value of a current that flows among the plurality of electrodes 21d, and measures the concentration of the medicinal solution 11 that contacts the measuring surface 21a based on the measurement value. Since the principles of concentration measurement as well as the configuration with respect to the concentration meter 21 of this kind are well-known, a detailed description is omitted herein.

The endoscope reprocessor 1 also includes an operation portion 13 and an output portion 14 which configure a user interface for exchanging information with a user. The operation portion 13 and the output portion 14 are electrically connected to the control portion 2. Note that the operation portion 13 and the output portion 14 may also be of a form that is equipped with an electronic device that is configured to perform radio communication with the control portion 2.

The operation portion 13 includes an operation member such as a push switch or a touch sensor. The output portion 14, for example, includes a display apparatus that is configured to display images or characters, a light emitting apparatus that is configured to emit light, or a speaker that is configured to emit sound, or a combination of these.

Figure 3:
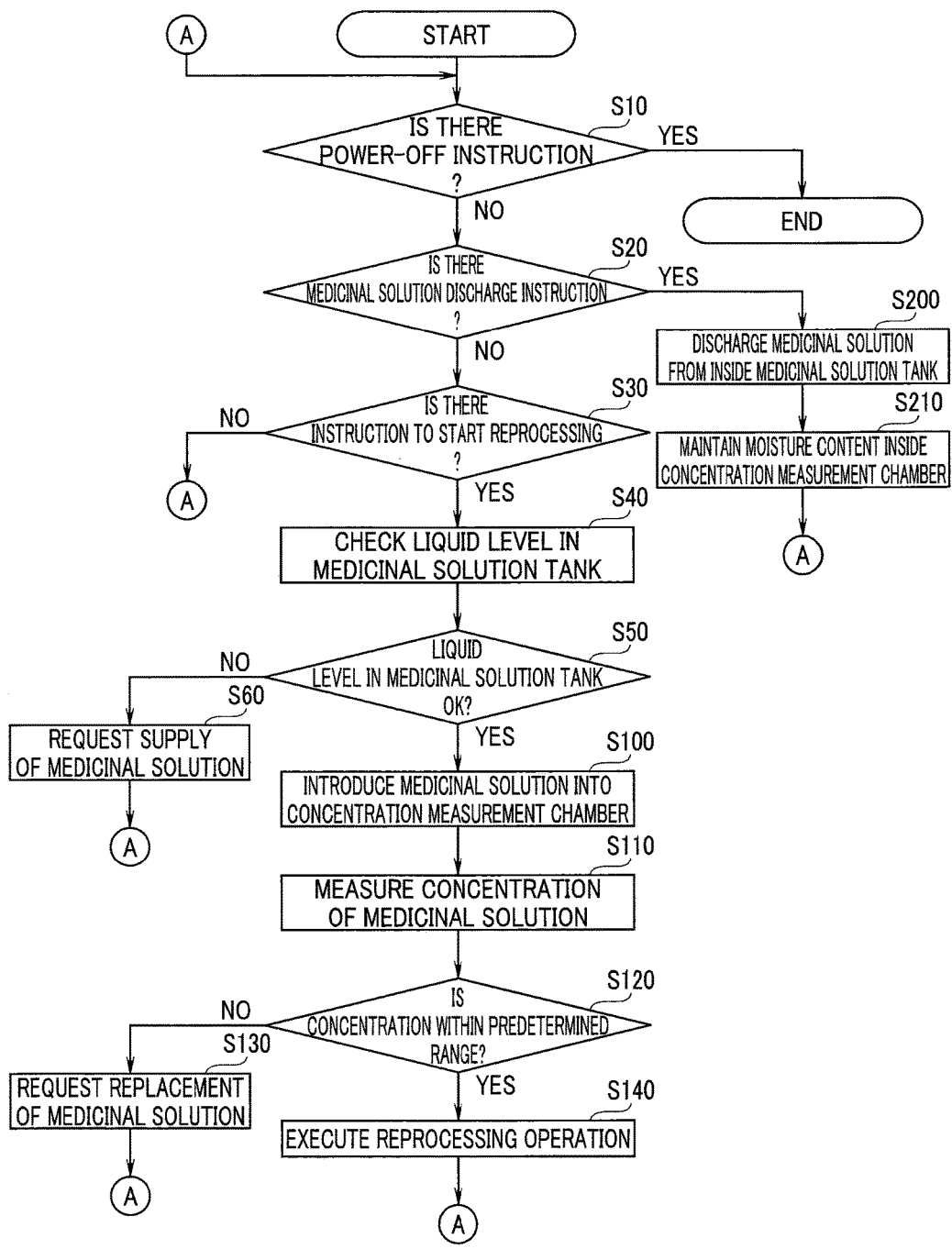
FIG. 3 is a flowchart illustrating a control method for an endoscope reprocessor according to the first embodiment.

Next, a control method for the endoscope reprocessor 1 having the aforementioned configuration will be described referring to the flowchart illustrated in FIG. 3. The processing flow illustrated in FIG. 3 is started when the power of the endoscope reprocessor 1 is placed in an "on" state by a manual operation performed by a user or by an automatic operation performed by means of timer control. Note that inputting of operation instructions to the endoscope reprocessor 1 by a user is performed through the operation portion 13.

After the power of the endoscope reprocessor 1 is placed in an "on" state, first, an initialization operation of each component is executed, and thereafter, as shown in steps S10 to S30, a standby state is entered in which the endoscope reprocessor 1 stands by until an instruction is inputted by the user.

Specifically, in step S10, it is determined whether or not an instruction to turn off the power was inputted by the user. If it is determined in step S10 that an instruction to turn off the power was inputted, the endoscope reprocessor 1 transitions to a power-off state and ends the processing flow illustrated in FIG. 3. In step S10, if it is determined that an instruction to turn off the power was not inputted, the processing transitions to step S20.

In step S20, it is determined whether or not the user inputted an instruction to discharge the medicinal solution 11 inside the medicinal solution tank 10 from the endoscope reprocessor 1. An operation to discharge the medicinal solution 11 from the endoscope reprocessor 1 is executed, for example, in a case of replacing the medicinal solution 11 inside the medicinal solution tank 10 or in a case where the endoscope reprocessor 1 will not be used for a comparatively long time period.

If it is determined in step S20 that an instruction to discharge the medicinal solution 11 inside the medicinal solution tank 10 was inputted, the processing transitions to step S200 that is described later to execute a discharge process. On the other hand, if it is determined in step S20 that an instruction to discharge the medicinal solution 11 inside the medicinal solution tank 10 was not inputted, the processing transitions to step S30.

In step S30, it is determined whether or not an instruction to execute reprocessing with respect to an endoscope was inputted by the user. If it is determined in step S30 that an instruction to execute reprocessing was inputted, the processing transitions to step S40 that is described later. On the other hand, if it is determined in step S30 that an instruction to execute reprocessing was not inputted, the processing returns to step S10.

In step S40, the liquid level gauge 10f is used to check whether or not the medicinal solution 11 is accumulated up to a predetermined liquid level inside the medicinal solution tank 10. If it is determined in step S40 that the medicinal solution 11 is not accumulated up to the predetermined liquid level inside the medicinal solution tank 10 ("No" in step S50), the processing transitions to step S60.

In step S60, a request to the user to supply the medicinal solution 11 into the medicinal solution tank 10 is outputted through the output portion 14. After execution of step S60, the processing returns to step S10. That is, in the endoscope reprocessor 1 of the present embodiment, reprocessing of an endoscope is not started until the medicinal solution 11 is supplied up to a predetermined liquid level inside the medicinal solution tank 10 by the user.

If it is determined in step S40 that the medicinal solution 11 is accumulated up to the predetermined liquid level inside the medicinal solution tank 10, ("Yes" in step S50), the processing transitions to step S100. That is, after step I that is a process of introducing the medicinal solution 11 into the medicinal solution tank 10 is executed, the processing transitions to step S100.

In step S100, the medicinal solution transfer portion 22 is activated to introduce the medicinal solution 11 from inside the medicinal solution tank 10 into the concentration measurement chamber 20. Specifically, in step S100, the open/close valve 22d is placed in an open state and operation of the introducing pump 22b is started. By this means, the medicinal solution 11 inside the medicinal solution tank 10 is introduced into the concentration measurement chamber 20. As a result of executing step S100, the measuring surface 21a of the concentration meter 21 that is disposed inside the concentration measurement chamber 20 contacts the medicinal solution 11.

Subsequently, in step S110, measurement of the concentration of the medicinal solution 11 is executed by means of the concentration meter 21. That is, in step S100 and step S110, step II that is a process of introducing the medicinal solution 11 into the concentration measurement chamber 20 and measuring the concentration of the medicinal solution 11 is executed.

Next, in step S120, it is determined whether or not the measurement value for the concentration of the medicinal solution 11 is within a predetermined range. The predetermined range of the concentration is a range in which the medicinal solution 11 exerts a medicinal efficacy required to execute reprocessing.

If it is determined in step S120 that the measurement value for the concentration of the medicinal solution 11 is within the predetermined range, the processing transitions to step S140 to execute reprocessing with respect to the endoscope. The reprocessing with respect to the endoscope includes a disinfecting treatment of introducing the medicinal solution 11 into the treatment tank 4 and immersing the endoscope in the medicinal solution 11.

In the disinfecting treatment, after the switching valve 7 is placed in a closed state, the medicinal solution pump 5b is operated to transfer the medicinal solution 11 from inside the medicinal solution tank 10 to inside the treatment tank 4 in which the endoscope is disposed. Subsequently, the medicinal solution pump 5b is stopped after the medicinal solution 11 has been accumulated up to a predetermined liquid level inside the treatment tank 4, and operation of the circulation pump 6*b* is then performed for a predetermined time period. Thereafter, after the circulation pump 6*b* is stopped, the switching valve 7 is placed in a state which allows the discharge conduit 9 and the recovery conduit 8 to communicate, and the medicinal solution 11 inside the treatment tank 4 is thereby recovered into the medicinal solution tank 10.

After the end of the reprocessing in step S140, the processing returns to step S10.

On the other hand, if it is determined in step S120 that the measurement value for the concentration of the medicinal solution 11 is outside the predetermined range, the processing transitions to step S130. In step S130, the output portion 14 is used to output a request to the user to execute an operation to replace the medicinal solution 11 by discharging the medicinal solution 11 inside the medicinal solution tank 10 and newly supplying unused medicinal solution 11 into the medicinal solution tank 10. After executing step S130, the processing returns to step S10.

That is, according to the endoscope reprocessor 1 of the present embodiment, reprocessing with respect to an endoscope is not started until the medicinal solution 11 having a concentration that is within a predetermined range is accumulated inside the medicinal solution tank 10.

As described above, to replace the medicinal solution 11 in the medicinal solution tank 10, the user inputs an instruction through the operation portion 13 to discharge the medicinal solution 11 inside the medicinal solution tank 10 from the endoscope reprocessor 1.

In the aforementioned step S20, if it is determined that an instruction to discharge the medicinal solution 11 inside the medicinal solution tank 10 from the endoscope reprocessor 1 was inputted by the user, the processing transitions to step S200.

In step S200, the discharge valve 10*e* is placed in an open state, and the medicinal solution 11 in the medicinal solution tank 10 is discharged to outside the endoscope reprocessor 1 via the medicinal solution discharge port 10*d*. After the medicinal solution 11 inside the medicinal solution tank 10 has been discharged, the discharge valve 10*e* is placed in a closed state.

After the execution of step S200, the inside of the medicinal solution tank 10 remains in an empty state until unused medicinal solution 11 is newly supplied via the medicinal solution supply portion 10*b*. That is, in step S200, a step III that is a process in which the medicinal solution 11 in the medicinal solution tank 10 is drained from the endoscope reprocessor 1 and a state in which the inside of the medicinal solution tank 10 is empty is maintained for a predetermined time period is executed.

Further, in step S200 of the present embodiment, operation of the introducing pump 22*b* of the medicinal solution transfer portion 22 is performed to discharge the medicinal solution 11 from inside the concentration measurement chamber 20 into the medicinal solution tank 10.

Next, in step S210, the open/close valve 22*d* of the medicinal solution transfer portion 22 is placed in a closed state and the introducing pump 22*b* is placed in a stopped state to thereby seal the internal space of the concentration measurement chamber 20.

Although execution of step S210 is started at a time that is after the medicinal solution 11 has been discharged from inside the concentration measurement chamber 20, the state is one in which moisture such as vapor or droplets of the medicinal solution 11 remains inside the concentration measurement chamber 20. Subsequently, by executing step S210 to seal the inside of the concentration measurement chamber 20, movement of the moisture such as vapor or droplets of the medicinal solution 11 that remains inside the concentration measurement chamber 20 to outside of the concentration measurement chamber 20 is prevented.

Therefore, according to the endoscope reprocessor 1 of the present embodiment, the moisture content inside the concentration measurement chamber 20 is maintained at a predetermined value or more by execution of step S210. In other words, by executing step S210, the relative humidity inside the concentration measurement chamber 20 is maintained at a predetermined value or more.

Although the predetermined value is not particularly limited and can be set as appropriate, for example, preferably the predetermined value is a relative humidity of 100% or more. This is because if the relative humidity is 100% or more, condensation is liable to occur on the measuring surface 21*a* of the concentration meter 21.

As described in the foregoing, the open/close valve 22*d* maintains a closed state even when the power of the endoscope reprocessor 1 is in an "off" state. The time when the open/close valve 22*d* changes to an open state is in step S100 which is after the medicinal solution 11 is accumulated inside the medicinal solution tank 10.

That is, according to the endoscope reprocessor 1 of the present embodiment, step IV that is a process that maintains the moisture content inside the concentration measurement chamber 20 at a predetermined value or more is executed during step III that is a process that maintains a state in which the inside of the medicinal solution tank 10 is empty for a predetermined time period.

According to the control method of the endoscope reprocessor 1 of the present embodiment that is described above, during a period in which the inside of the medicinal solution tank 10 is empty, the concentration measurement chamber 20 is sealed and movement of moisture inside the concentration measurement chamber 20 to outside the concentration measurement chamber 20 is prevented. By this means, according to the present embodiment, during a period in which the medicinal solution 11 has been discharged and the inside of the medicinal solution tank 10 is empty also, since the relative humidity inside the concentration measurement chamber 20 is maintained at a predetermined value or more, drying of the measuring surface 21*a* of the concentration meter 21 can be prevented and the measuring surface 21*a* can be kept in a wet state.

For example, according to the control method for the endoscope reprocessor 1 of the present embodiment, after replacing the medicinal solution 11 inside the medicinal solution tank 10, since measurement of the concentration of the medicinal solution 11 by the concentration meter 21 can be executed without setting a waiting time, the time period required to perform reprocessing for an endoscope can be shortened.

Figure 4:
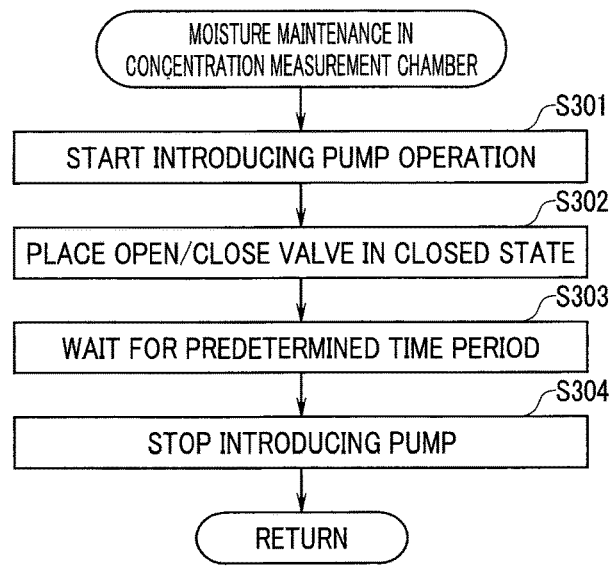
FIG. 4 is a flowchart illustrating a modification of the control method for an endoscope reprocessor 1 according to the first embodiment.

FIG. 4 illustrates a modification of the control method for the endoscope reprocessor 1 of the present embodiment. FIG. 4 is a flowchart for describing the process (step IV) that maintains the moisture content inside the concentration measurement chamber 20 at the predetermined value or more, which is executed in step S210.

In the process that maintains the moisture content inside the concentration measurement chamber 20 at the predetermined value or more of the present modification, first, in step S301, operation of the introducing pump 22*b* of the medicinal solution transfer portion 22 is started. Note that, if operation of the introducing pump 22*b* is already being performed in step S200, in step S301 the operating state of the introducing pump 22*b* is maintained.

Next, in step S302, the open/close valve 22d is placed in a closed state. Subsequently, in step S303, the endoscope reprocessor 1 stands by for a predetermined time period. Since air is introduced into the sealed concentration measurement chamber 20 by executing step S302 and step S303, the air pressure inside the concentration measurement chamber 20 becomes a positive pressure that is higher than the atmospheric pressure.

Next, in step S304, the introducing pump 22b is stopped. Because the inside of the concentration measurement chamber 20 is sealed even when the introducing pump 22b is stopped, the air pressure inside the concentration measurement chamber 20 is kept at a positive pressure.

Thus, according to the present modification, in the process of maintaining the moisture content inside the concentration measurement chamber 20 at a predetermined value or more, the air pressure inside the concentration measurement chamber 20 is made higher than the atmospheric pressure. As a result of the air pressure inside the concentration measurement chamber 20 rising, the dew-point temperature of the medicinal solution 11 that is the liquid remaining inside the concentration measurement chamber 20 increases. Consequently, according to the present modification, it becomes difficult for liquid that remains in the concentration measurement chamber 20 to evaporate and thus dispersion of moisture to outside of the concentration measurement chamber 20 is suppressed. It is therefore possible for the moisture content inside the concentration measurement chamber 20 to be maintained at a predetermined value or more for a longer time period.

Second Embodiment

Figure 5:
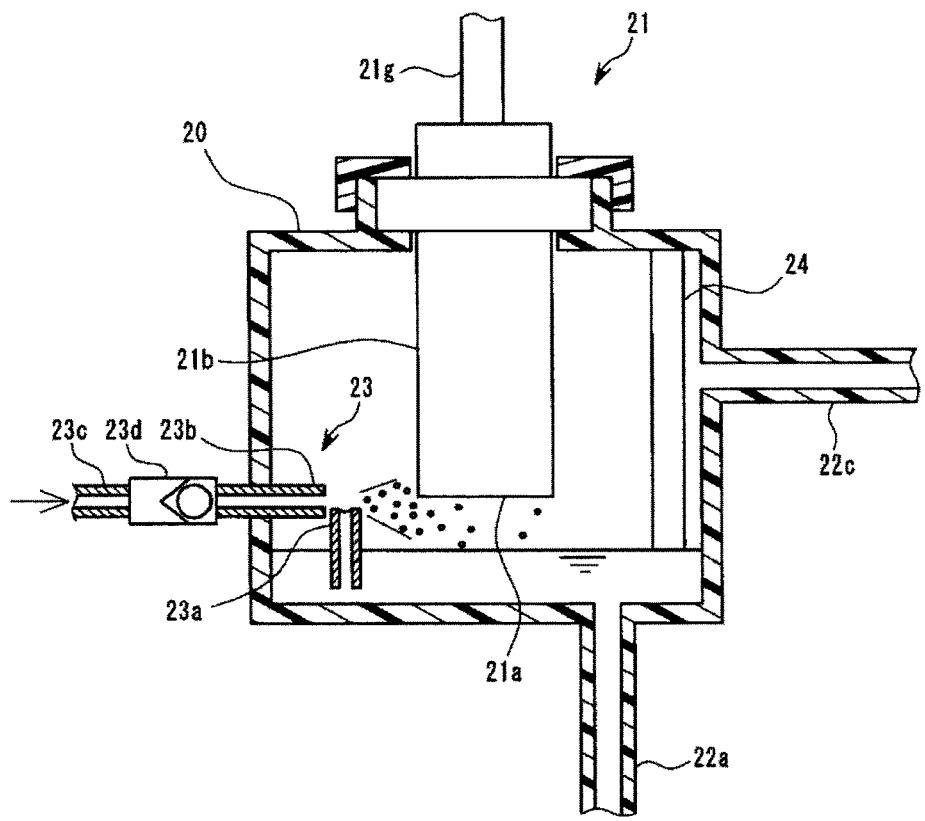
FIG. 5 is a cross-sectional diagram illustrating the configuration of a concentration measurement chamber according to a second embodiment.

Next, a second embodiment of the present invention will be described. Hereunder, only differences with respect to the first embodiment are described, and components that are the same as components in the first embodiment are denoted by the same reference numerals and a description of such components is omitted as appropriate. FIG. 5 is a view illustrating the configuration of the concentration measurement chamber 20 of the endoscope reprocessor 1 of the present embodiment.

As shown in FIG. 5, an atomization portion 23 is arranged in the concentration measurement chamber 20 of the present embodiment. The atomization portion 23 disperses liquid that is accumulated in the concentration measurement chamber 20 into the air inside the concentration measurement chamber 20 as minute droplets.

As one example according to the present embodiment, the atomization portion 23 has the configuration of an atomizer that uses a so-called "Venturi effect". The atomization portion 23 includes a narrow tube portion 23a that is configured to suck up liquid accumulated inside the concentration measurement chamber 20, and an air blowing portion 23b that is configured to blow air at an upper end portion of the narrow tube portion 23a to generate a flow of air having a predetermined velocity.

The air blowing portion 23b is connected via an air supply conduit 23c to, for example, an air supply apparatus such as an air tank or an air compressor that is configured to deliver air at a predetermined pressure which is included in the endoscope reprocessor 1. A check valve 23d that is configured to block the flow of air or liquid in the direction from the concentration measurement chamber 20 to the air supply conduit 23c is provided in the air supply conduit 23c. Note that the atomization portion 23 may also include a valve that is configured to discharge air that was fed into the concentration measurement chamber 20.

In a state in which liquid is accumulated up to a predetermined liquid level inside the concentration measurement chamber 20, the atomization portion 23 of the present embodiment sucks up the liquid and thereafter disperses the liquid as minute droplets into the air inside the concentration measurement chamber 20 by blowing air that is supplied from the air supply apparatus at the upper end portion of the narrow tube portion 23a. Further, the inside of the concentration measurement chamber 20 is sealed by the check valve 23d when the supply of air from the air supply apparatus is stopped.

Note that the configuration of the atomization portion 23 is not limited to the configuration described in the present embodiment. For example, the atomization portion 23 may have a configuration that disperses liquid accumulated inside the concentration measurement chamber 20 by causing the inner wall face of the concentration measurement chamber 20 to vibrate by means of an ultrasound transducer or the like. Further, for example, the atomization portion 23 may have a configuration that disperses liquid accumulated inside the concentration measurement chamber 20 by agitating the liquid.

A liquid level sensor 24 is provided inside the concentration measurement chamber 20 of the present embodiment. The liquid level sensor 24 detects whether or not the level of liquid accumulated inside the concentration measurement chamber 20 reaches a predetermined liquid level. The liquid level sensor 24 is electrically connected to the control portion 2, and outputs information regarding a detection result to the control portion 2.

The configuration of the liquid level sensor 24 is not particularly limited. The liquid level sensor 24 may be a so-called "electrode-type liquid level sensor" which, for example, includes a pair of electrodes that are arranged apart from each other, and detects whether or not the liquid surface reaches a predetermined liquid level based on the presence or absence of electrical conductivity between the pair of electrodes. Further, for example, the liquid level sensor 24 may be a so-called "float-type liquid level sensor" that is configured to detect whether or not the liquid surface reaches a predetermined liquid level based on the operational state of a switch that is configured to open and close in accordance with vertical motion of a float that floats in the liquid.

Next, a control method for the endoscope reprocessor 1 of the present embodiment will be described. Note that the control method for the endoscope reprocessor 1 of the present embodiment differs from the first embodiment only with respect to a process (step IV) which maintains the moisture content inside the concentration measurement chamber 20 at a predetermined value or more that is executed in step S210. Hence, hereunder, only the process that maintains the moisture content inside the concentration measurement chamber 20 at a predetermined value or more of the present embodiment is described.

Figure 6:
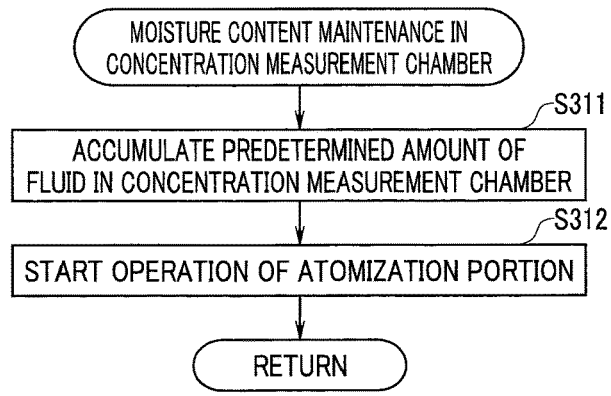
FIG. 6 is a flowchart of a process that maintains a moisture content inside the concentration measurement chamber of the second embodiment at a predetermined value or more.

As shown in the flowchart in FIG. 6, in the process for maintaining the moisture content inside the concentration measurement chamber 20 at a predetermined value or more of the present embodiment, first, in step S311, liquid is accumulated inside the concentration measurement chamber 20 until reaching a predetermined liquid level by means of the liquid level sensor 24.

In step S311, the kind of liquid that is accumulated inside the concentration measurement chamber 20 is not particularly limited, and may be the medicinal solution 11 or may be a different liquid to the medicinal solution 11, for example, water.

For example, in a case where the liquid accumulated inside the concentration measurement chamber 20 is the medicinal solution 11, when the medicinal solution 11 is discharged from inside the concentration measurement chamber 20 in step S200, part of the medicinal solution 11 is caused to remain inside the concentration measurement chamber 20.

Further, for example, in a case where the liquid accumulated inside the concentration measurement chamber 20 is water, after water supplied from a water supply facility or the like has been introduced into the treatment tank 4, the water is introduced into the concentration measurement chamber 20 via the recovery conduit 8, the medicinal solution tank 10 and the introduction conduit 22a.

Next, in step S312, operation of the atomization portion is started to disperse liquid accumulated in the concentration measurement chamber 20 into the air inside the concentration measurement chamber 20 as minute droplets. Operation of the atomization portion may be continuously performed or may be performed intermittently at predetermined time intervals.

Thus, according to the endoscope reprocessor 1 of the present embodiment, during step III that is a process which maintains a state in which the inside of the medicinal solution tank 10 is empty for a predetermined time period, step IV is executed which is a process that accumulates a predetermined amount of liquid inside the concentration measurement chamber 20 and disperses the liquid as minute droplets into the air inside the concentration measurement chamber 20.

According to the above described control method for the endoscope reprocessor 1 of the present embodiment, during a period in which the inside of the medicinal solution tank 10 is empty, by dispersing liquid as minute droplets inside the concentration measurement chamber 20, drying of the measuring surface 21a of the concentration meter 21 can be prevented and the measuring surface 21a can be maintained in a wet state.

For example, according to the control method for the endoscope reprocessor 1 of the present embodiment, after replacing the medicinal solution 11 inside the medicinal solution tank 10, an operation to measure the concentration of the medicinal solution 11 can be executed by the concentration meter 21 without setting a waiting time, and hence a time period required to perform reprocessing with respect to an endoscope can be shortened.

Note that, according to the present embodiment, although in step S311 a configuration is adopted in which the liquid level sensor 24 is used for accumulating a predetermined amount of liquid inside the concentration measurement chamber 20, a configuration for accumulating a predetermined amount of liquid inside the concentration measurement chamber 20 in step S311 is not limited to the aforementioned configuration.

Figure 7:
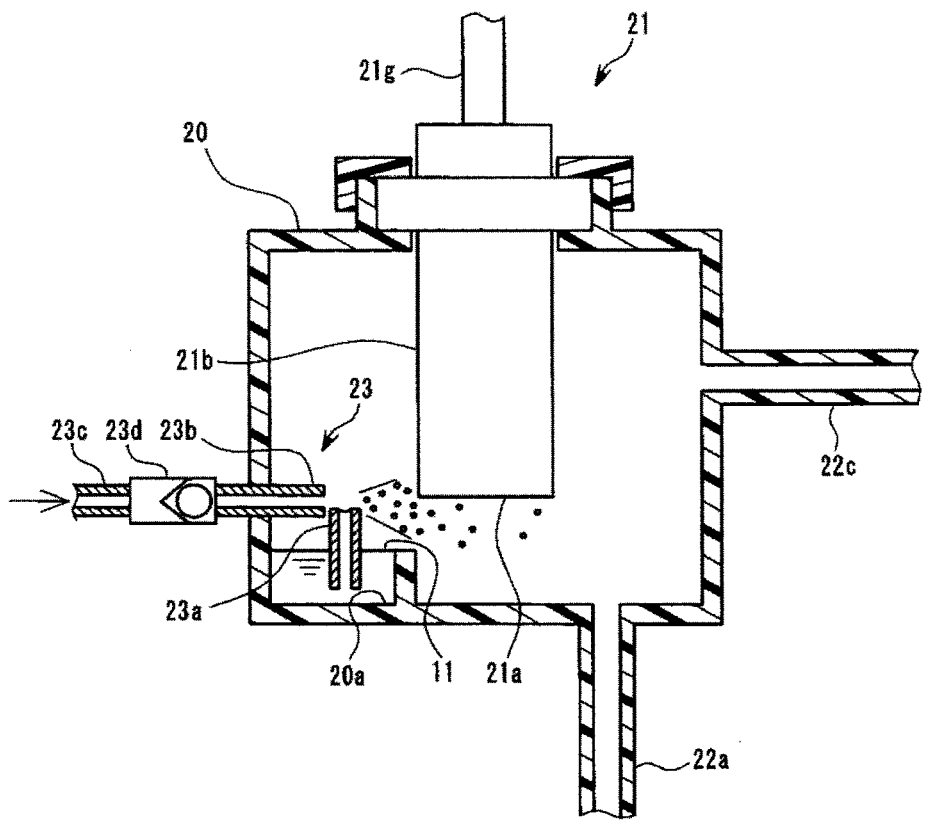
FIG. 7 is a cross-sectional diagram illustrating a modification of the concentration measurement chamber of the second embodiment.

FIG. 7 illustrates a modification of the configuration for accumulating a predetermined amount of liquid inside the concentration measurement chamber 20 in step S311. According to the modification illustrated in FIG. 7, a concave portion 20a that is a downwardly concave shape is provided on a bottom face portion of the concentration measurement chamber 20. After executing the process that discharges the medicinal solution 11 from inside the concentration measurement chamber 20 in step S200, a part of the medicinal solution 11 remains inside the concave portion 20a. The atomization portion 23 disperses the medicinal solution 11 that is accumulated inside the concave portion 20a into the air inside the concentration measurement chamber 20 as minute droplets.

Note that, in present embodiment also, similarly to the modification of the first embodiment, in the process that maintains the moisture content inside the concentration measurement chamber 20 at a predetermined value or more, the air pressure inside the concentration measurement chamber 20 may be made higher than the atmospheric pressure.

Third Embodiment

Next, a third embodiment of the present invention will be described. Hereunder, only differences with respect to the first embodiment are described, and components that are the same as components in the first embodiment are denoted by the same reference numerals and a description of such components is omitted as appropriate.

The control method for the endoscope reprocessor 1 of the present embodiment differs from the first embodiment only with respect to the process (step IV) which maintains the moisture content inside the concentration measurement chamber 20 at a predetermined value or more that is executed in step S210. Hence, hereunder, only the process that maintains the moisture content inside the concentration measurement chamber 20 at a predetermined value or more of the present embodiment is described.

Figure 8:
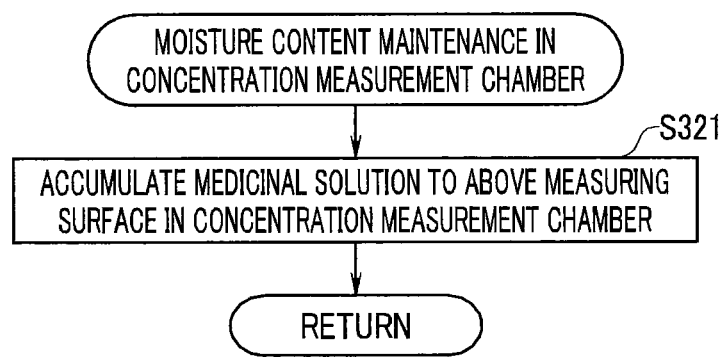
FIG. 8 is a flowchart of a process that maintains a moisture content inside a concentration measurement chamber of a third embodiment at a predetermined value or more.

As shown in the flowchart in FIG. 8, in the process that maintains the moisture content inside the concentration measurement chamber 20 at a predetermined value or more of the present embodiment, in step S321, the medicinal solution 11 is accumulated up to a predetermined liquid level inside the concentration measurement chamber 20. The predetermined liquid level to which the medicinal solution 11 is accumulated inside the concentration measurement chamber 20 in step S321 is located above the measuring surface 21a of the concentration meter 21 that is disposed inside the concentration measurement chamber 20.

Thus, according to the endoscope reprocessor 1 of the present embodiment, during step III that is a process which maintains a state in which the inside of the medicinal solution tank 10 is empty for a predetermined time period, step IV is executed which is a process that accumulates the medicinal solution 11 up to a liquid level that is higher than the measuring surface 21a of the concentration meter 21 inside the concentration measurement chamber 20 to thereby immerse the measuring surface 21a in the medicinal solution 11.

According to the above described control method for the endoscope reprocessor 1 of the present embodiment, during a period in which the inside of the medicinal solution tank 10 is empty, by immersing the measuring surface 21a of the concentration meter 21 in the medicinal solution 11, drying of the measuring surface 21a can be prevented and the measuring surface 21a can be maintained in a wet state.

For example, according to the control method for the endoscope reprocessor 1 of the present embodiment, after replacing the medicinal solution 11 inside the medicinal solution tank 10, an operation to measure the concentration of the medicinal solution 11 can be executed by the concentration meter 21 without setting a waiting time, and hence a time period required to perform reprocessing with respect to an endoscope can be shortened.

The present invention is not limited to the above described embodiments, and may be suitably changed without departing from the gist or concept of the invention readable from the appended claims and the entire specification, and a control method for an endoscope reprocessor with such changes is also included in the technical scope of the present invention.

What is claimed is:

1. A control method for an endoscope reprocessor that includes a medicinal solution tank, a concentration measurement chamber, and a concentration meter which is disposed in the concentration measurement chamber and which comprises a container, an electrode that is housed inside the container, a permeable membrane configured to seal the container, and a content fluid that is sealed inside the container, the control method comprising:
- a step I of introducing a medicinal solution into the medicinal solution tank;
- a step II of introducing the medicinal solution into the concentration measurement chamber and measuring a concentration of the medicinal solution;
- a step III of draining the medicinal solution inside the medicinal solution tank from the endoscope reprocessor, and maintaining a state in which inside of the medicinal solution tank is empty for a predetermined time period; and
- a step IV of maintaining a moisture content inside the concentration measurement chamber at a predetermined value or more during the step III.

2. The control method for an endoscope reprocessor according to claim 1, wherein:
in the step IV, inside of the concentration measurement chamber is maintained in a sealed state.

3. The control method for an endoscope reprocessor according to claim 2, wherein:
in the step IV, a relative humidity inside the concentration measurement chamber is maintained at a predetermined value or more.

4. The control method for an endoscope reprocessor according to claim 3, wherein:
in the step IV, an air pressure inside the concentration measurement chamber is maintained in a state in which the air pressure is higher than atmospheric pressure.

5. The control method for an endoscope reprocessor according to claim 1, wherein:
in the step IV, a state in which a predetermined amount of liquid is accumulated inside the concentration measurement chamber is maintained.

* * * * *